United States Patent [19]

Glicksman et al.

[11] Patent Number: 5,468,872
[45] Date of Patent: Nov. 21, 1995

[54] K-252A FUNCTIONAL DERIVATIVES POTENTIATE NEUROTROPHIN-3 FOR THE TREATMENT OF NEUROLOGICAL DISORDERS

[75] Inventors: Marcie A. Glicksman, Swarthmore; David P. Rotella, Downington; Nicola Neff, Rose Valley, all of Pa.; Chikara Murakata, Tokyo, Japan

[73] Assignees: Cephalon, Inc., West Chester, Pa.; Kyowa Hakko Kogyo Co., Ltd., Tokyo, Japan

[21] Appl. No.: 122,893

[22] Filed: Sep. 16, 1993

[51] Int. Cl.$^6$ .................................................. C07D 487/12
[52] U.S. Cl. ........................................... 548/416; 548/417
[58] Field of Search ...................................... 548/416, 417

[56] References Cited

U.S. PATENT DOCUMENTS

| | | |
|---|---|---|
| 4,735,939 | 4/1988 | McCoy et al. . |
| 4,816,450 | 3/1989 | Bell et al. . |
| 4,877,776 | 10/1980 | Murakata et al. . |
| 5,093,330 | 3/1992 | Caravatti et al. . |
| 5,231,001 | 7/1993 | Kaplan et al. . |

FOREIGN PATENT DOCUMENTS

| | | | |
|---|---|---|---|
| 328000 | 8/1989 | European Pat. Off. | 548/416 |
| 3835842 | 4/1990 | Germany | 548/416 |
| 60-257652 | 6/1987 | Japan . | |
| 60-295173 | 7/1987 | Japan . | |
| 60-295172 | 7/1987 | Japan . | |
| 62-327859 | 12/1988 | Japan . | |
| 62-327858 | 12/1988 | Japan . | |
| WO93/00909 | 1/1993 | WIPO . | |
| WO93/08809 | 5/1993 | WIPO . | |
| 93-24490 | 12/1993 | WIPO | 548/416 |
| 93-24491 | 12/1993 | WIPO | 548/416 |

OTHER PUBLICATIONS

Berg et al., "K–252a Inhibits Nerve Growh Factor–induced trk Proto–oncogene Tyrosine Phosphorylation and Kinase Activity," The Journal of Biological Chemistry 267:13–16, 1992.

Borasio, "Differential effects of the protein kinase inhibitor K–252a on the in vitro survival of chick embryonic neurons," Neuroscience Letters 108:207–212, 1990.

Bottenstein et al., "Growth of a rat neuroblastoma cell line in serum–free supplemented medium," Proc. Natl. Acad. Sci. USA 76:514–517, 1979.

Collazo et al., "Cellular Targets and Trophic Functions of Neurotrophin–3 in the Developing Rat Hippocampus," Neuron 9:643–656, 1992.

Coussens et al., "Multile, Distinct Forms of Bovine and Human Protein Kinase C Suggest Diversity in Cellular Signaling Pathways," Science 233:859–866, 1986.

Doherty et al., "K–252a specifically inhibits the survival and morphological differentiation of NGF–dependent neurons in primary cultures of human dorsal root ganglia," Neuroscience Letters 96:1–6, 1989.

Fonnum, "A rapid radiochemical method for the determination of choline acetyltransferase," Journal of Neurochemistry 24:407–409, 1975.

Fraser, "Expressin of Eucaryotic Genes in Insect Cell Cultures," In Vitro Cellular & Development Biology 25:225≧235, 1989.

Glicksman et al., "K–252a and Staurosporine Promote Choline Acetyltransferase Activity in Rat Spinal Cord Cultures," Journal of Neurochemistry 61:210–221, 1993.

Hallböök et al., "Evolutionary Studies of the Nerve Growth Factor Family Reveal a Novel Member Abundantly Expressed in Xenopus Ovary," Neuron 6:845–858, 1991.

Ishida et al., "Effect of Depolarizing Agents on Choline Acetyltransferase and Acetylcholinesterase Activities in Primary Cell Cultures of Spinal Cord," The Journal of Neuroscience 3:1818–1823, 1983.

Kase et al., "K–252 Compounds, Novel and Potent Inhibitors of Protein Kinase C and Cyclic Nucleotide–Dependent Protein Kinases," Biochemical and Biophysical Research Communications 142:436–440, 1987.

Klein et al., "trkB, a novel tyrosine protein kinase receptor expressed during mouse neural development", The EMBO Journal 8:3701–3709, 1989.

Klein et al., "The Trk Proto–Oncogene Encodes A Receptor for Nerve Growth Factor," Cell 65:189–197, 1991.

Knüsel et al., "K–252b Selectively Potentiates Cellular Actions and trk Tyrosine Phosphorylation Mediated by Neurotrophin–3," Journal of Neurochemistry 59:715–722, 1992.

Koizumi et al., "K–252a: A Specific Inhibitor of the Action of Nerve Growth factor on PC12 Cells," The Journal of Neuroscience 8:715–721, 1988.

Laemmli, "Cleavage of Structural Proteins during the Assembly of the Head of Bacteriophage T4," Nature 227:680–685, 1970.

Lamballe et al., "trC, a New Member of the trk Family of Tyrosine Protein Kinases, Is a Receptor for Neurotrophin–3," Cell 66:967–979, 1991.

Levi–Montalcini, "Development Neurobiology and the Natural History of Nerve Growth Factor," Ann. Rev. Neurosci. 5:341–62, 1982.

Lewis et al., "Is K252a a Non–Competitive Partial Agonist of High Affinity NGF Receptors?" Society for Neuroscience, Abstract, 1:13, 1992.

Maisonpierre et al., "Neurotrophin–3: A Neurotrophic Factor Related to NGF and BDNF," Science 247:1446–51, 1990.

Matsuda et al., "Inhibition by K–252a, a new inhibitor of protein kinase, of nerve growth factor–induced neurite outgrowth of chick embryo dorsal root ganglion cells," Neuroscience Letters 87:11–17, 1988.

(List continued on next page.)

Primary Examiner—Jacqueline Haley
Attorney, Agent, or Firm—Richard P. Burgoon, Jr.; Fish & Richardson

[57] ABSTRACT

Functional K-252a derivatives are used to enhance trk phosphorylation and to potentiate the activity of neurotrophin-3 (NT-3). These compounds can be used to treat neurological disorders, alone or in combination with NT-3.

3 Claims, 7 Drawing Sheets

OTHER PUBLICATIONS

McManaman et al., "Development Discord among Markers for Cholinergic Differentiation: In Vitro Time Courses for Early expression and Responses to Skeletal Muscle Extract," Developmental Biology 125:311–320, 1988.

Moody et al., "Synthesis of the Staurosporine Aglycon," J. Org. Chem. 57:2105–2114, 1992.

Morrissey, "Silver Stain for Proteins in Polyacrylamide Gels: A Modified Procedure with Enhanced Uniform Sensitivity," Analytical Biochemistry 117:307–310, 1981.

Nakanishi et al., "K–252b, c and d, Potent Inhibitors of Protein Kinase C from Microbial Origin," The Journal of Antibiotics 39:1066–1071, 1986.

Ohmichi et al., "Inhibition of the Cellular Actions of Nerve Growth Factor by Staurosporine and K252A Results from the Attenuation of the Activity of the trk Tyrosine Kinase," Biochemistry 31:4034–4039, 1992.

Nye et al., "K–252a and Staurosporine Selectively Block Autophosphorylation of Neurotrophin Receptors and Neurotrophin–Mediated Response," Molecular Biology of the Cell 3:677–686, 1992.

Smith et al., "Molecular Engineering of the *Autographa californica* Nuclear Polyhedrosis Virus Genome: Deletion Mutations within the Polyhedrin Gene," Journal of Virology 46:584–593, 1983.

Steglich et al., "Indole Pigments from the Fruiting Bodies of the Slime Mold *Arcyria denudata*," Angew. Chem. Int. Ed. Engl. 19:459–460, 1980.

Compounds Active in NT-3 Potentiation
of ChAT Activity in Basal Forebrain Cultures

| Compound | ChAT Activity (%NT3) Basal Forebrain Cultures | | |
|---|---|---|---|
| | 10nM | 100nM | 300nM |
| II-1 | inactive | 115 | 131 |
| II-2 | inactive | inactive | 139 |
| I-1 | 172 | 136 | toxic |
| I-2 | 138 | 142 | 108 |
| I-3 | 135 | 148 | 130 |
| I-4 | 120 | 149 | 146 |
| I-5 | 115 | 150 | 150 |
| I-6 | 146 | 183 | 183 |
| III-1 | 120 | 120 | 119 |
| I-7 | 121 | inactive | toxic |
| I-8 | 118 | 132 | 120 |
| I-9 | 128 | 160 | 172 |
| I-10 | 120 | 188 | 185 |
| I-11 | 163 | inactive | inactive |
| I-12 | 153 | inactive | inactive |
| I-13 | 172 | 141 | toxic |
| I-14 | 155 | 181 | 181 |
| I-15 | 159 | 177 | 176 |
| II-3 | inactive | 142 | 148 |
| II-4 | inactive | 130 | 129 |
| I-16 | 143 | 196 | 206 |
| II-5 | inactive | 122 | 151 |
| I-17 | 154 | 176 | 127 |
| I-18 | inactive | 123 | 149 |
| I-19 | inactive | 113 | 116 |
| I-20 | 112 | 128 | 127 |
| I-21 | 165 | 143 | inactive |
| III-2 | 159 | 181 | 177 |

FIG. 3

Compounds Active in NT-3
Potentiation of DRG Neuronal Survival

| Compound | DRG neuronal survival (%NT3) 100nM |
|---|---|
| II-2 | 162 |
| I-4 | 134 |
| I-6 | 174 |
| I-10 | 178 |
| I-14 | 159 |
| I-15 | 182 |
| II-3 | 148 |
| I-16 | 154 |

FIG. 6

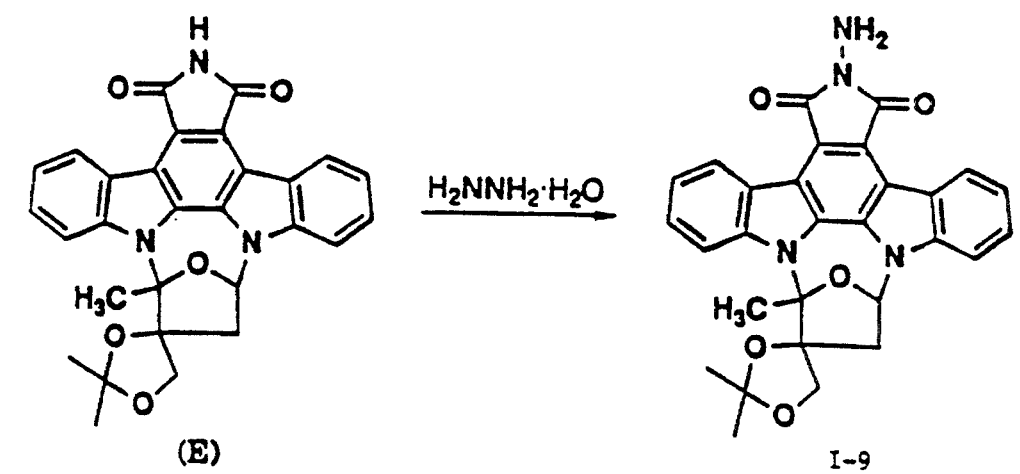
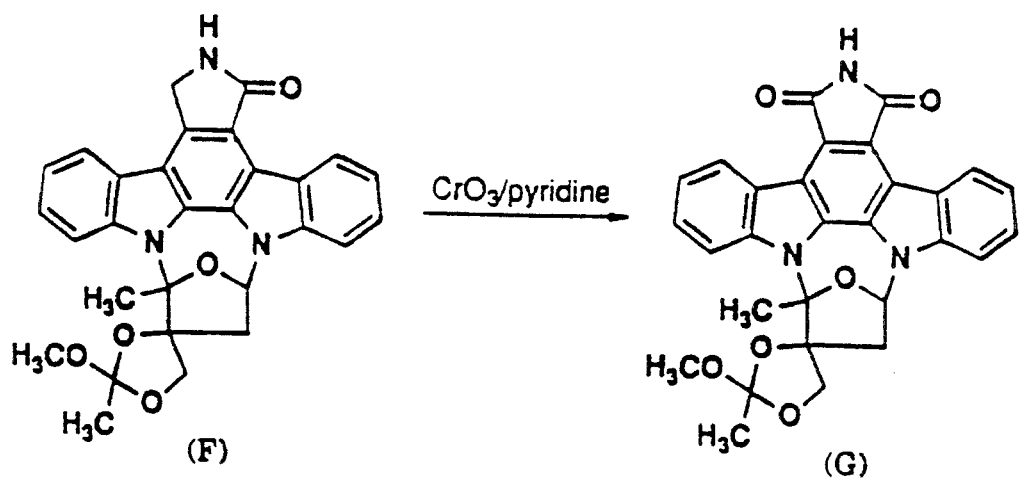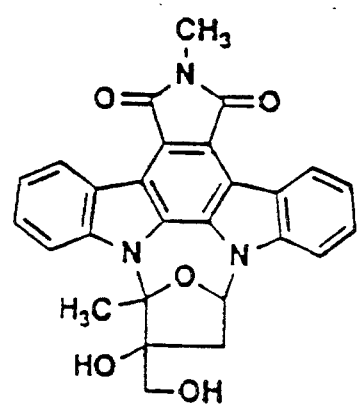
FIG. 8

K-252A FUNCTIONAL DERIVATIVES POTENTIATE NEUROTROPHIN-3 FOR THE TREATMENT OF NEUROLOGICAL DISORDERS

BACKGROUND OF THE INVENTION

This invention concerns functional K-252a derivatives that potentiate the activity of neurotrophins.

The etiology of neurodegenerative disorders is unknown. Such disorders may involve neurotrophins, which are low molecular weight polypeptides that play a role in the development, function, or survival of responsive cells.

Nerve growth factor (NGF) is the best characterized neurotrophin and is required for normal development and function of certain sensory, and cholinergic neurons (Levi-Montalcini, *Annu. Rev. Neurosci.* 5:341-362, 1982). Less is known about other neurotrophins, such as neurotrophin-3 (NT3), due in part to inadequate knowledge concerning the structure, function or binding properties of NT-3 responsive cell receptors. NT-3 plays a role in the survival and function of cholinergic neurons in the basal forebrain (Knusel et al., *J. Neurochem.* 59:715-722, 1992) and hippocampal neurons (Collazo et. al., *Neuron* 9:643-656, 1992), and, like NGF, may influence the survival or function of many cell types. NT-3, among other neurotrophins, exhibits characteristic patterns of activity in the nervous system (Maisonpierre et al., *Science* 247:1446-1451, 1991) which depends, in part, on productive cell receptor interactions.

The high affinity neurotrophic receptors, trks, comprise a family of proteins consisting of trk A, trk B, and trk C (see Knusel et al., supra). Members of this receptor family are membrane associated proteins that exhibit tyrosine kinase activity. Interaction of a neurotrophin ligand with trks induces the phosphorylation of specific tyrosine residues on the receptor. Phosphorylation of trks is an immediate response to neurotrophin binding. It is an absolute requirement for the activation of enzymatic pathways regulating functional responses to the neurotrophins by the cell (Klein et al., *Cell* 65:189-197, 991; Lamballe et al., *Cell* 66:967-979, 1991).

Ethical (implanting fetal cells producing endogenous and/or recombinant neurotrophin) and technical (ability to produce large quantities of pure neurotrophin) considerations limit the full therapeutic value of neurotrophins in the treatment of neurological disease. These considerations may prevent widespread use of NT-3 or other neurotrophins. Thus, new molecules that potentiate the neurotrophin activity are of special interest.

K-252a is an indolocarbazole alkaloid that was originally isolated from a *Nocardiopsis sp.* culture (Kase et al., *J. Antibiotics* 39:1059-1065, 1986). It is an inhibitor of several enzymes, including protein kinase C (Kase et al., *Biochem. Biophys. Res. Comm.* 142:436-440, 1987; Nakanishi et al., *J. Biol. Chem.* 263:6215-6219, 1988), and trk (Berg et al., *J. Biol. Chem.* 267:13-16, 1992). Consistent with this latter effect, K-252a blocks NGF mediated cell survival in some in vitro cell assays (Koizumi et al., *J. Neurosci.* 8: 715-721, 1988; Doherty et al., *Neurosci. Lett.* 96:1-6, 1989; Matsuda et al., *Neurosci. Lett.* 87:11-17, 1988), but not in other assay systems (Borasio, *Neurosci. Lett.* 108:207-212, 1990). K-252a will induce neurotrophin-like effects in certain neuronal cell types, but the chemically related K-252b will not (see Knusel et al. supra). These findings imply that multiple proteins interact with K-252a (Coussens et al., *Science* 233:859-866, 1986). It is likely that such complex interactions are responsible for the conflicting data found in the prior art.

K-252a and K-252b influence the phosphorylation state of trks. For example, K-252a may inhibit neurotrophin receptor phosphorylation (Squinto et al. WO 93/00909). However, in some settings, K-252a and K-252b potentiate target cell actions and trk tyrosine phosphorylation mediated by NT-3 (Knusel et. al. supra). K-252a may be a non-competitive partial agonist of trks (Lewis et al., *Society for Neuroscience*, Abstract, 1:13, 1992).

The proposed uses of K-252a or related K-252a derivatives such as staurosporine include tumor inhibition (Murakata et al., U.S. 4,877,776; Nomoto et al. EPO 238, 011; Caravatti et al., U.S. 5,093,330;), anti-insecticidal activity (McCoy et al., U.S. 4,735,939), and inhibition of inflammation (Bell et al., U.S. Pat. No. 4,816,450).

SUMMARY OF THE INVENTION

In general, the invention features a method for potentiating the ability of a neurotrophin, preferably NT-3, to promote the survival or function of a neurotrophin-responsive cell by contacting the neurotrophin-responsive cell with a functional K-252a derivative of any one of formulae I-III:

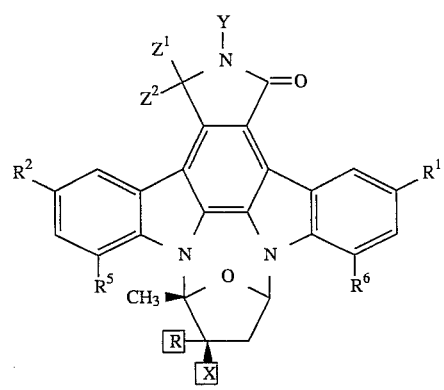

wherein:

a) $Z^1$ and $Z^2$ together represent O; each $R^1$, $R^2$, $R^5$, and $R^6$, independently is H, F, Cl, Br, I, $NO_2$, CN, alkyl of 1–6 carbons, or $NR^{13}R^{14}$ where each $R^{13}$ and $R^{14}$ independently is H or n-alkyl of 1–6 carbons;

Y is H, OH, $NH_2$, n-alkyl of 1–6 carbons, CHO, benzyl, O-n-alkyl of 1–6 carbons, $(CH_2)_nOH$ or $(CH_2)_nNH_2$ where n is an integer of 1–6; then either 1) R is OH, or O-n-alkyl of 1–6 carbons; and X is $CH_2OH$, $CH_2NH_2$, (or an acid salt thereof;) $CH_2O$-n-alkyl of 2–7 carbons, $CO_2R^7$ where $R^7$ is H or alkyl of 1–6 carbons, $CONH(CH_2)_nOR^8$ where n is an integer of 1–6 and $R^8$ is H or an acyl derivative group, or $CONHR^9$ where $R^9$ is alkyl of 1–3 carbons; or 2) R and X are combined to form a linking group of the formula $-CH_2OCR^{10}R^{11}O-$ where each $R^{10}$ and $R^{11}$ independently is H or alkyl of 1–3 carbons; or $-CH_2NR^{12}CO_2-$ where $R^{12}$ is H or alkyl of 1–3 carbons;

or b) $Z^1$ is H and $Z^2$ is OH; Y is H or CHO; R is OH; and X is CONH$(CH_2)_2OH$, $CO_2CH_3$, or $CH_2OH$; and $R^1$, $R^2$, $R^5$ and $R^6$ are as defined in a);

or c) $Z^1$ and $Z^2$ are both H and R, Y, and X are as defined in b), except that X cannot be $CO_2CH_3$; and when $R^1$ is Br, X cannot be $CH_2OH$; and $R^1$, $R^2$, $R^5$ and $R^6$ are as defined in a);

d) $Z^1$ is H and $Z^2$ is $SR^{15}$ where $R^{15}$ is n-alkyl of 1–3 carbons; and Y, R and X are defined as in b), except that when $R^{15}$ is $C_2H_5$, X cannot be $CH_2OH$; and $R^1$, $R^2$, $R^5$ and $R^6$ are as defined in a).

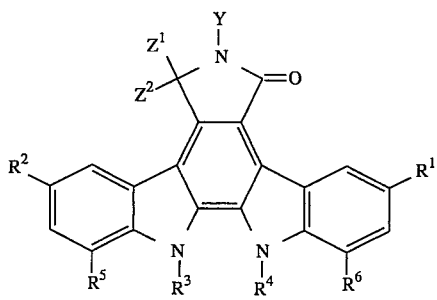

II.

wherein:

a) $Z^1$ and $Z^2$ together represent O, then either
1) each $R^1$, $R^2$, $R^5$, and $R^6$ independently is H, F, Cl, Br, I, $NO_2$, CN, alkyl of 1–6 carbons, or $NR^{13}R^{14}$ where each $R^{13}$ and $R^{14}$, independently, is H or n-alkyl of 1–6 carbons; and
Y is H, OH, $NH_2$, n-alkyl of 1–6 carbons, CHO, benzyl, O-n-alkyl of 1–6 carbons, $(CH_2)_nOH$ or $(CH_2)_nNH_2$ where n is an integer of 1–6; and each $R^3$ and $R^4$ independently is H or $(CH_2)_nCH(OH)CH_2OH$, where n is an integer of 1–6;

or 2) each $R^1$, $R^2$, $R^3$, $R^4$, $R^5$ and $R^6$ independently is H; and Y is as defined in a) 1), except that Y cannot be benzyl;

or b) $Z^1$ is H and $Z^2$ is H, OH, or $SR^{15}$, where $R^{15}$ is n-alkyl of 1–3 carbons; Y is H or CHO; and each $R^1$, $R^2$, $R^3$, $R^4$, $R^5$, $R^6$ independently is H.

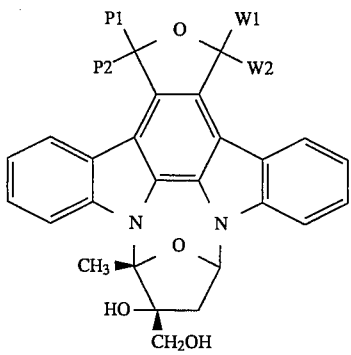

III.

wherein:

a) each P1 and P2 is H or P1 and P2 together represent O and each W1 and W2 is H or W1 and W2 together represent O provided that each P1 and P2 is different from W1 and W2.

In a related aspect, the invention features a method for potentiating the ability of a neurotrophin, preferably NT-3, to promote the survival or function of a cholinergic or a sensory neuron by contacting said neuron with a functional K-252a derivative of the formula:

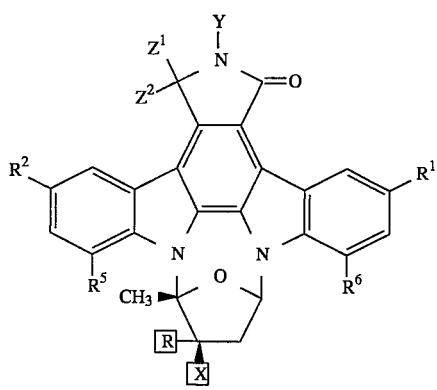

wherein:

a) $Z^1$ and $Z^2$ together represent O and each $R^5$ and $R^6$ independently is H;
1) Y is H, $OCH_3$, $NH_2$, $CH_3$, $CH_2CH_2OH$, or OH; and R is OH or $OCH_3$; and
X is $CO_2 R^7$, where $R^7$ is H or alkyl of 1–6 carbons, $CH_2OH$, CONH ($CH_2)_2OH$, $CONHCH_3$, or $CH_2NH_2 \cdot HCl$ and each $R^1$ and $R^2$ is H; or
2) Y is H, $OCH_3$, $NH_2$, $CH_3$, $CH_2CH_2OH$ or OH; and R and X are combined to form a linking group of the formulae: $—CH_2OC(CH_3)_2O—$, $—CH_2NHCO_2—$, $—CH_2N(CH_3) CO_2—$, or $—CH_2N(C_2H_5) CO_2—$; and each $R^1$ and $R^2$ is H;

or

3) Y is H;
R is OH;
X is $CO_2CH_3$; and each $R^1$ and $R^2$ is Br;

or b) $Z^1$ is H and $Z^2$ is H OH or $SC_2H_5$; and each $R^1$ $R^2$ $R^5$ and $R^6$ is H;
Y is H;
R is OH, and
X is $CONH(CH_2)_2OH$, $CH_2OH$ or $CO_2CH_3$; except that when $Z^2$ is H, X cannot be $CO_2CH_3$.

In a related aspect, the invention features a method for potentiating the ability of a neurotrophin, preferably NT-3, to promote the survival or function of a cholinergic or a sensory neuron by contacting said neuron with a functional K-252a derivative of the formula:

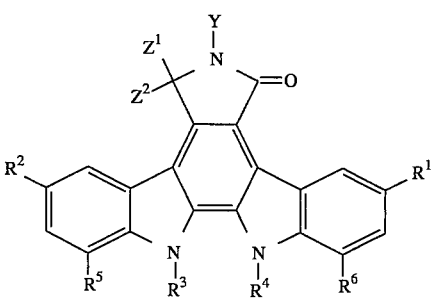

wherein:

a) $Z^1$ and $Z^2$ together represent O; and each $R^1$, $R^2$, $R^5$, $R^6$ is H; then either
1) Y is H, or $CH_3$; and each $R^3$, $R^4$, is H;

or

2) Y is $CH_3$; and $R^3$ is $CH_2CH (OH) CH_2OH$; and $R^4$ is H or $CH_2CH(OH)CH_2OH$;
and b) $Z^1$ is H and $Z^2$ is H; Y is CHO; and each $R^1$, $R^2$, $R^3$, $R^4$, $R^5$, and $R^6$ is H.

In a related aspect, the invention features a method for potentiating the ability of a neurotrophin, preferably NT-3, to promote the survival or function of a cholinergic or a sensory neuron by contacting said neuron with a functional K-252a derivative of the formula:

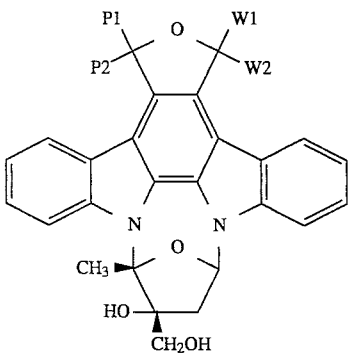

wherein:

a) each P1 and P2 is H or P1 and P2 together represent O and each W1 and W2 is H or W1 and W2 together represent O provided that each P1 and P2 is different from W1 and W2.

In a related aspect, the invention features a method for potentiating the ability of a neurotrophin, preferably NT-3, to promote the survival of a sensory neuron by contacting said neuron with a functional K-252a derivative of the formula:

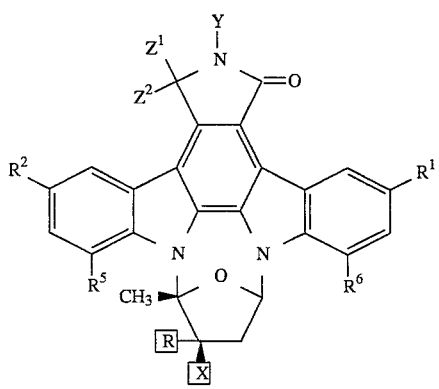

wherein:

a) $Z^1$ and $Z^2$ together represent O and each $R^5$, and $R^6$ independently is H; then either 1) Y is H, $NH_2$, $CH_3$, $CH_2CH_2OH$, OH; and
R is OH; and
X is $CO_2R^7$, where $R^7$ is H or alkyl of 1-6 carbons, $CH_2OH$, CONH $(CH_2)_2OH$, $CONHCH_3$, $CH_2NH_2 \cdot HCl$; and each
$R^1$ and $R^2$ is H; or (2) Y is H, $NH_2$, $CH_3$, $CH_2CH_2OH$, or OH; and
R and X together represent: $-CH_2OC(CH_3)_2O-$, $-CH_2NHCO_2-$, $-CH_2N(CH_3)CO_2-$, or $-CH_2N(C_2H_5)CO_2-$; and each $R^1$ and $R^2$ is H;
or 3) Y is H;

R is OH;
X is $CO_2CH_3$; and
each $R^1$ and $R^2$ is Br;

or b) $Z^1$ is H and $Z^2$ is H, OH, $SC_2H_5$ and each $R^1$, $R^2$, $R^5$ and $R^6$ is H;
Y is H;
R is OH; and
X is $CH_2OH$ or $CO_2CH_3$; except that when $Z^2$ is H, X cannot be $CO_2CH_3$.

In a related aspect, the invention features a method for potentiating the ability of a neurotrophin, preferably NT-3, to promote the survival of a sensory neuron by contacting said neuron with a functional K-252a derivative of the formula:

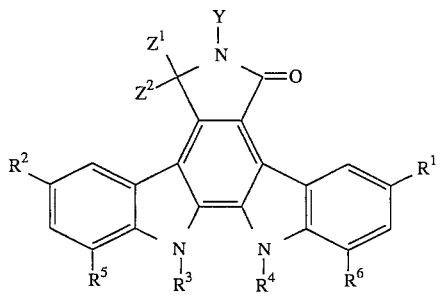

wherein:

a) $Z^1$ and $Z^2$ together represent O and each $R^1$, $R^2$, $R^5$, $R^6$ is H;

1) Y is H or $CH_3$; and each R3 and R4 is H;
or

2) Y is $CH_3$; and
$R^3$ is $CH_2CH(OH) CH_2OH$; and
$R^4$ is H or $CH_2CH(OH)CH_2OH$;
and b) $Z^1$ is H and $Z^2$ is H;
Y is CHO; and
each $R^1$, $R^2$, $R^3$, $R^4$, $R^5$, $R^6$, is H In a related aspect, the invention features a method for potentiating the ability of a neurotrophin, preferably NT-3, to promote the survival of a sensory neuron by contacting said neuron with a functional K-252a derivative of the formula:

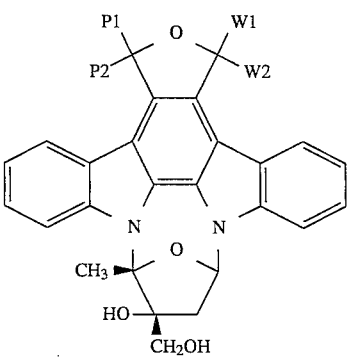

wherein:

a) each P1 and P2 is H or P1 and P2 together represent 0; and each W1 and W2 is H or W1 and W2 together represent O; provided that each P1 and P2 is different from W1 and W2.

Preferred compounds are those represented by any one of formulae I, II, and III where the following substitutions are made:

TABLE 1

| Compound[1] | Y | X | R | $Z^1Z^{2(2)}$ |
|---|---|---|---|---|
| II-1 | CHO | — | — | H, H |
| II-2 | H | — | — | O |
| I-1 | H | $CO_2CH_3$ | OH | O |
| I-2 | H | $CO_2n\text{-}C_3H_7$ | OH | O |
| I-3 | H | $CO_2n\text{-}C_4H_9$ | OH | O |
| I-4 | H | $CO_2n\text{-}C_6H_{13}$ | OH | O |
| I-5 | $OCH_3$ | $CO_2CH_3$ | $OCH_3$ | O |
| I-6[3] | H | $CO_2CH_3$ | OH | O |
| III-1[7] | — | $CH_2OH$ | OH | — |
| I-7 | H | $CONH(CH_2)_2OH$ | OH | H, H |
| I-8[6] | H | $-CH_2OC(CH_3)_2O-$ | — | O |
| I-9[6] | $NH_2$ | $-CH_2OC(CH_3)_2O-$ | — | O |
| I-10 | $NH_2$ | $CH_2OH$ | OH | O |
| I-11 | H | $CONHCH_3$ | OH | O |
| I-12[6] | H | $-CH_2NHCO_2-$ | — | O |
| I-13[6] | H | $-CH_2N(CH_3)CO_2-$ | — | O |
| I-14 | $CH_3$ | $CH_2OH$ | OH | O |
| I-15 | $CH_2CH_2OH$ | $CH_2OH$ | OH | O |
| II-3[4] | $CH_3$ | — | — | O |
| II-4[5] | $CH_3$ | — | — | O |
| I-16 | $NH_2$ | $CH_2NH_2\cdot HCl$ | OH | O |
| II-5 | $CH_3$ | — | — | O |
| I-17 | OH | $CH_2OH$ | OH | O |
| I-18 | H | $CO_2CH_3$ | OH | H, OH |
| I-19 | H | $CO_2CH_3$ | OH | H, $SC_2H_5$ |
| I-20 | H | $CH_2OH$ | OH | H, OH |
| I-21[6] | H | $-CH_2N(C_2H_5)CO_2-$ | — | O |
| III-2[8] | — | $CH_2OH$ | OH | — |

[1]$R^1$ and $R^2$ are H except as noted in [3]; $R^5$ and $R^6$ are H; $R^3$ and $R^4$ are H except as noted in [4] and [5].
[2]$Z^1$ and $Z^2$ are as noted, or both are combined together to represent oxygen, where indicated.
[3]$R^1$ and $R^2$ are both Br.
[4]$R^3$ is $CH_2CH(OH)CH_2OH$ and $R^4$ is H.
[5]$R^3$ and $R^4$ are both $CH_2CH(OH)CH_2OH$.
[6]X and R are combined together to form the linking group.
[7]P1, P2 are combined together to represent O; W1, W2 = H.
[8]P1, P2 = H; W1, W2 are combined together to represent O.

Particularly preferred compounds for use in potentiating the ability of a neurotrophin, preferably NT-3, to promote the survival or function of a cholinergic or sensory neuron are those represented by any one of formulae I and II where the following substitutions are made:

TABLE 2

| Compound[1] | Y | X | R | $Z^1Z^{2(2)}$ |
|---|---|---|---|---|
| II-2 | H | — | — | O |
| I-4 | H | $CO_2n\text{-}C_6H_{13}$ | OH | O |
| I-6[3] | H | $CO_2CH_3$ | OH | O |
| I-10 | $NH_2$ | $CH_2OH$ | OH | O |
| I-14 | $CH_3$ | $CH_2OH$ | OH | O |
| I-15 | $CH_2CH_2OH$ | $CH_2OH$ | OH | O |
| II-3[4] | $CH_3$ | — | — | O |
| I-16 | $NH_2$ | $CH_2NH_2\cdot HCl$ | OH | O |

[1]$R^1$ and $R^2$ are H except as noted in [3]; $R^4$, $R^5$, and $R^6$ are H; $R^3$ is H except as noted in [4].
[2]$Z^1$ and $Z^2$ are both combined to represent oxygen.
[3]$R^1$ and $R^2$ are both Br.
[4]$R^3$ is $CH_2CH(OH)CH_2OH$.

The invention also includes a method for treating nerve cell degeneration by administering a therapeutic amount of a functional K-252a derivative alone or in combination with a neurotrophin, preferably NT-3. Nerve cell degeneration is a feature of many neurological diseases including, but not limited to, Alzheimer's disease; motor neuron disease, e.g., amyotrophic lateral sclerosis; Parkinson's disease; cerebrovascular disease, e.g., stroke and other ischemic injuries; Huntington's disease; AIDS dementia; epilepsy; concussive or penetrating injuries of the brain or spinal cord; peripheral neuropathies; and disorders induced by excitatory amino acids.

The invention also features a method for enhancing the phosphorylation of trks by administering a functional K252a derivative to neurotrophin responsive cells, alone or in combination with a neurotrophin, preferably NT-3.

The invention also features a compound represented by the following formula:

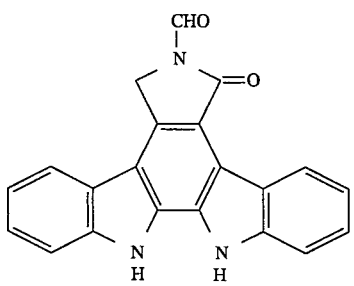

or a pharmaceutically acceptable salt thereof.

The invention also features a compound represented by the following formula:

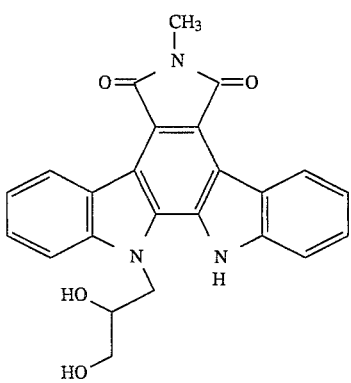

or a pharmaceutically acceptable salt thereof.

The invention also features a compound represented by the following formula:

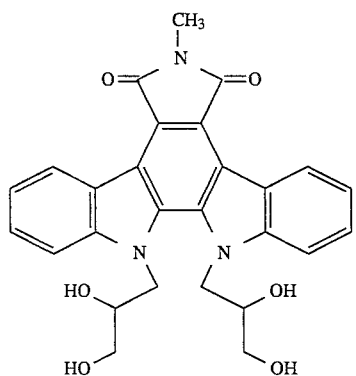

or a pharmaceutically acceptable salt thereof.

As detailed below, potentiation of neurotrophin activity and phosphorylation of trks by a functional K-252a derivative is characterized by: a) basal forebrain neuron choline acetyltransferase (CHAT) assay, b) dorsal root ganglion neuron survival assay, and c) PC-12 (pheochromocytoma-12, a malignant neuronal progenitor cell line) trk tyrosine phosphorylatiOn assay. ChAT catalyzes the synthesis of the neurotransmitter acetylcholine. It is considered a specific marker for functional cholinergic neurons. Neuron survival is assayed by quantitation of the selective uptake and enzymatic conversion of a dye by living neurons. Trk phosphorylation in PC-12 cells is identified by immunoprecipitation and blotting of trk complexes, followed by binding of receptor phosphotyrosine by a detectable antibody which binds phosphotyrosine. NT-3 biological activity is thus defined as the ability of a K252a functional derivative to increase ChAT activity, or promote neuron survival or enhance the phosphorylation of trk. These in vitro cell assays may reflect action of a K252a functional derivative in vivo.

Functional derivatives of K-252a as used herein, are chemically modified forms of K-252a that improve solubility, absorption, transport (e.g., through the blood-brain barrier and cellular membranes), biological half-life, decrease toxicity, or increase potency or efficacy.

Cholinergic neurons as defined herein, are basal forebrain neurons and other neurons in the central nervous system that use acetylcholine as a neurotransmitter.

Preferred sensory neurons as defined herein, are those of the dorsal root ganglion.

By enhancing or promoting the survival or function of a neuron is meant enhancing or promoting nerve cell survival, nerve fiber (axonal) growth, increasing enzymatic activity of nerve cells, or enhancing or promoting cell receptor phosphorylation.

Neurotrophin responsive cells as defined herein, are those cells that have trk and whose function and/or survival, is potentiated by a neurotrophin.

A neurotrophin as defined herein, is a low molecular weight polypeptide that enhances or promotes the survival or function of neurotrophin responsive neurons. Neurotrophins include NGF (nerve growth factor), NT-3 (neurotrophin-3), NT-4/5 (neurotrophin-4/5), brain derived neurotrophic factor (BDNF), ciliary neurotrophic factor (CNTF), basic fibroblast growth factor (bFGF), hippocampus-derived neurotrophic factor (HDNF), insulin and insulin-like factors.

Trks are defined herein as receptors for the neurotrophins.

Pharmaceutically acceptable salts, as defined herein, are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminum salt, and zinc salt. Examples of the pharmaceutically acceptable ammonium salts are ammonium salt and tetramethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

Other features and advantages of the invention will be apparent from the following description of the preferred embodiments thereof, and from the claims.

DESCRIPTION OF THE PREFERRED EMBODIMENTS

The drawings are first described.

BRIEF DESCRIPTION OF THE DRAWINGS

FIG. 3 is a table which shows K-252a functional derivatives that potentiate NT-3 ChAT activity in embryonic rat basal forebrain cultures.

FIG. 6 is a table illustrating K-252a functional derivatives that potentiate the ability of NT-3 to support dorsal root ganglion neuron survival in vitro.

FIG. 8 is a figure outlining the chemical synthesis of compounds I-9 and 1-14.

Synthesis of K-252a Functional Derivatives—

Figure 1:
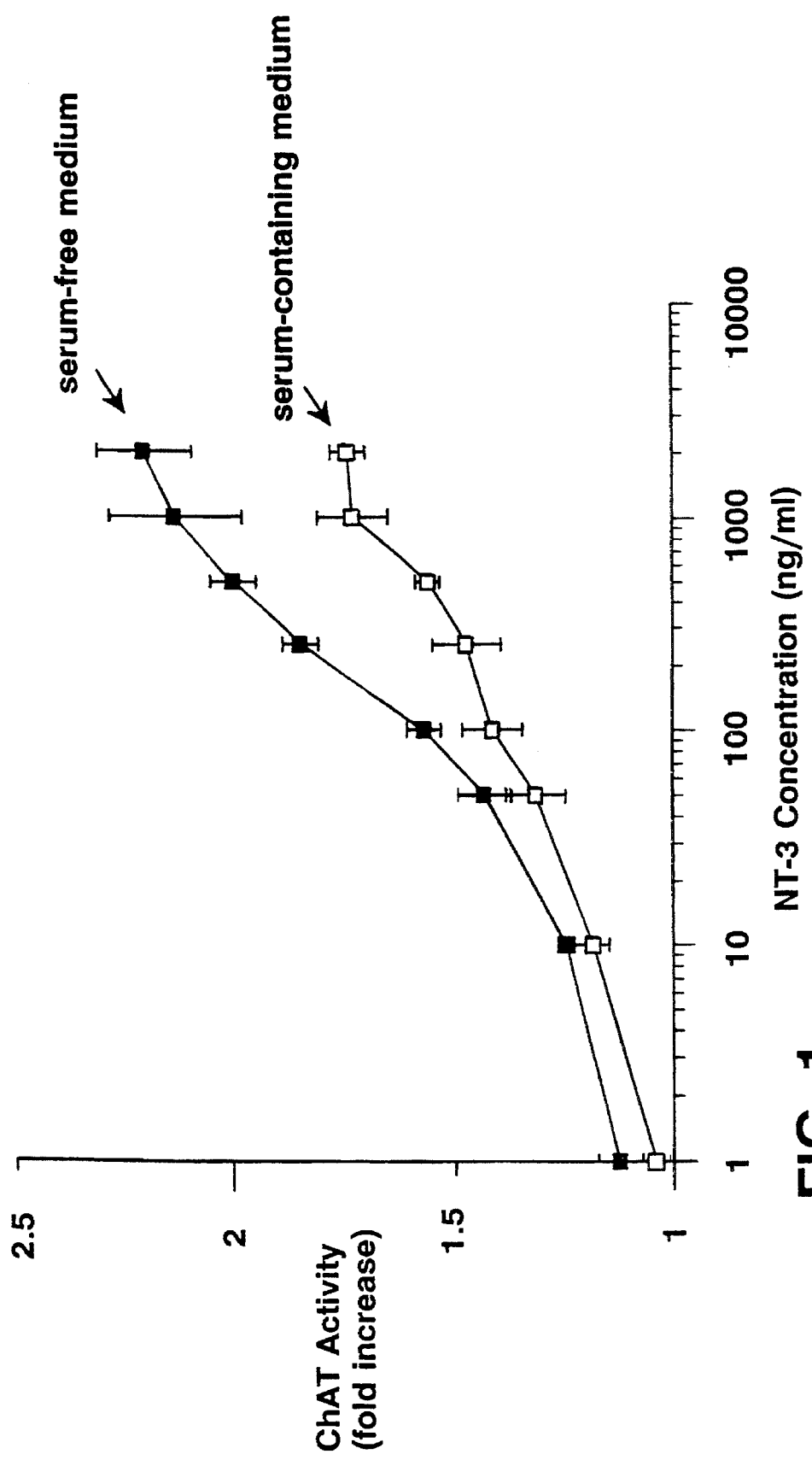
FIG. 1 is a graph which illustrates the dosage effect of NT-3 on ChAT activity in embryonic rat basal forebrain cultures.

The chemical synthesis of representative K-252a functional derivatives is outlined below. Additional functional derivatives of K-252a may be prepared de novo by chemical synthesis using methods known to those skilled in the art. For example, procedures used for preparation of the compound represented in Formula I are described by Murakata et al. (U.S. Pat. Nos. 4,923,986 and 4,877,776), hereby incorporated by reference. Procedures used for the preparation of the compound represented in Formula II are described by Moody et al., J. Org. Chem. 57: 2105-2114 (1992); Steglich et al., Angew. Chem. Int. Ed. Engl. 19: 459-460 (1980); Nakanishi et al., J. Antibiotics 39: 1066-1071 (1986); and Japanese Patent Application No. 60-295172 (1985). Further methods are described for the compounds in Japanese Patent Application Nos. 60-295173 (1985), 62-327858 (1987), 62-327859 (1987) and 60-257652 (1985) [Meiji Seika Kaisha Ltd.].

I. Chemical Synthesis and Analysis of Representative K-252a Derivatives

Compound numbers refer to K-252a derivatives listed in Table 1.

Preparation of Compound II-1

$POCl_3$ (0.28 ml, 3 mmol) and Compound (A) (311 mg, 1 mmol) were added to 20 ml of dimethylformamide under ice cooling, followed by stirring at 90° C. for 4 hours. The precipitates were collected by filtration, and washed successively with water and methanol to give 250 mg (yield 74%) of Compound II-1.

The starting material compound (A) has been disclosed J. Antibiot., 39:1072 (1986).

The following characteristic values may be obtained by nuclear magnetic resonance spectroscopy (NMR) or mass spectroscopy (MS):

$^1H$-NMR (DMSO-$d_6$) δ(ppm): 5,298(2H, s), 7.255-8.073(7H, m), 9.036(1H, d, J=7.7Hz), 9.300 (1H, s), 11.891 (1H, s) 12. 175 ( 1H, s) EI-MS (m/z) : 339 (M)$^+$

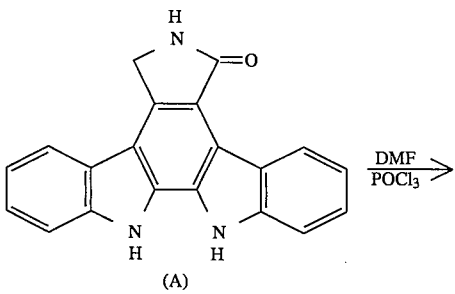

(A)

DMF / $POCl_3$ →

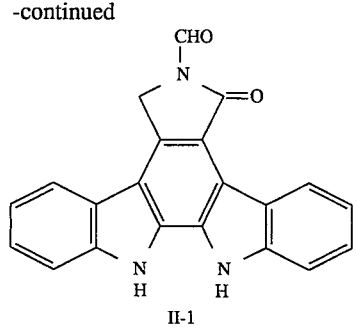

II-1

Preparation of Compound II-3

Compound (B) (208 mg, 0.61 mmol) was dissolved in 20 ml of tetrahydrofuran, and then 74 mg (1.83 mmol) of sodium hydride (60%) was added thereto, followed by stirring at room temperature for 10 minutes. Allyl bromide (0.063 ml, 0.73 mmol) was added thereto and the mixture was stirred at room temperature for 15 hours. To the solution was added a saturated aqueous solution of ammonium chloride, and the organic layer was washed with a saline solution and dried over magnesium sulfate. After evaporation of the solvent, the residue was subjected to silica gel column chromatography (chloroform) to give 135 mg (yield 58%) of Compound (C).

The following characteristic values for Compound C may be obtained by NMR:

$^1H$-NMR (CDCl$_3$+DMSO-$d_6$; 4/1) δ(ppm):3.04(3H, s), 4.80–5.20(4H, m) , 5.96–6.40(1H, m) ,7.28–7.72 (6H, m), 9.18(1H, d, J=8.0Hz), 9.20(1H, d, J=8.0Hz), 9.84(1H, s)

Compound (C) (145 mg, 0.38 mmol) was dissolved in a mixture of 7 ml of tetrahydrofuran and 0.5 ml of pyridine, and then 4 ml of tetrahydrofuran containing 200 mg of osmium tetroxide was added thereto, followed by stirring at room temperature for 6 hours. Sodium thiosulfate (348 mg), 7 ml of water, and 7 ml of pyridine were added to the reaction solution, followed by stirring at room temperature for 1 hour. To the solution was added tetrahydrofuran for dilution, and the mixture was washed with a saturated aqueous solution of sodium bicarbonate, and dried over magnesium sulfate. After evaporation of the solvent, the residue was subjected to silica gel column chromatography chloroform/methanol=97/3) to give 93 mg of Compound II-3.

The starting material Compound (B) has been disclosed in Tetrahedron, 48: 8869 ( 1992 ) .

The following characteristic values may be obtained by NMR and MS:

$^1H$-NMR (DMSO-$d_6$) δ (ppm):3.186(3H, s), 3.633(2H, m), 4.068(1H, brs), 4.804(1H, dd, J=7.9, 15.6Hz) , 4.955(1H, dd, J=3.2, 15.6Hz), 5.407(1H, d, J=4.9Hz), 5.480(1H, t, J=5.1Hz), 7.351-7.818(6H, m) , 9.093 (1H, d, J=7.9Hz) , 9.131(1H, dd, J=0.5, 7.9Hz), 11.736(1H, s) FAB-MS (m/z):414 (M+1)$^+$.

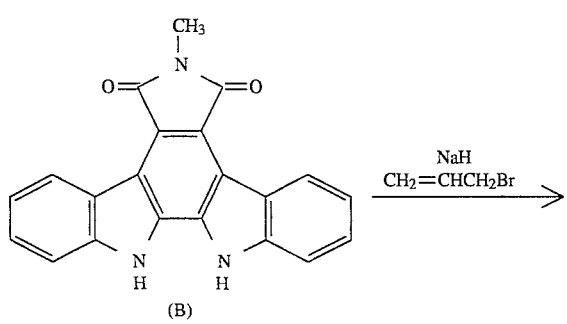

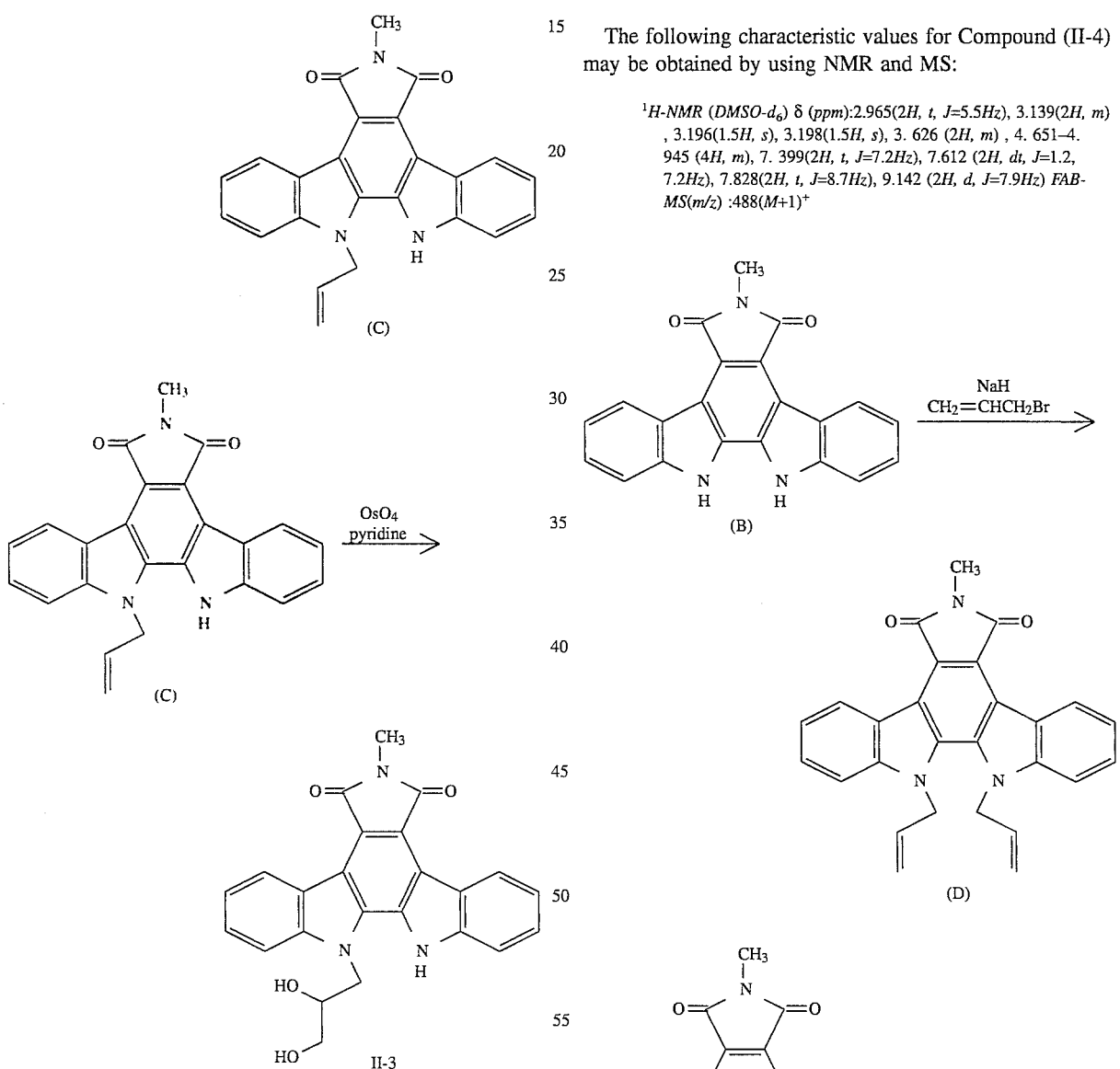

to 40° C.

Compound II-4 can be obtained by treatment of Compound (D) with 2 to 4 equivalents of an oxidant. An example of the oxidant is $OsO_4$. As a reaction solvent, a mixed solvent of tetrahydrofuran and pyridine or the like is used. The ratio of tetrahydrofuran to pyridine is 1/20 to 1/5. The reaction is completed in 3 to 8 hours at 0 to 40° C.

The following characteristic values for Compound (D) may be obtained by using NMR and MS:

$^1H$-NMR $(CDCl_3)\delta(ppm)$:3.21(3H, s), 4.92–6.40 (10H, m), 7.40–7.64 (6H, m), 9.32(2H, d, J=8.0Hz)EI-MS(m/z): 419 $(M)^+$ The following characteristic values for Compound (II-4) may be obtained by using NMR and MS:

$^1H$-NMR $(DMSO$-$d_6)$ δ $(ppm)$:2.965(2H, t, J=5.5Hz), 3.139(2H, m), 3.196(1.5H, s), 3.198(1.5H, s), 3. 626 (2H, m) , 4. 651–4. 945 (4H, m), 7. 399(2H, t, J=7.2Hz), 7.612 (2H, dt, J=1.2, 7.2Hz), 7.828(2H, t, J=8.7Hz), 9.142 (2H, d, J=7.9Hz) FAB-MS(m/z) :488$(M+1)^+$ Preparation of Compound II-4

Compound (D) can be prepared by reaction of Compound (B) with 2 to 4 equivalents of allyl bromide in the presence of 3 to 5 equivalents of a base. An example of the base is an alkali metal hydride such as sodium hydride. As a reaction solvent, tetrahydrofuran, dimethylformamide, or the like is used. The reaction is completed in 0.5 to 15 hours at −10°

-continued

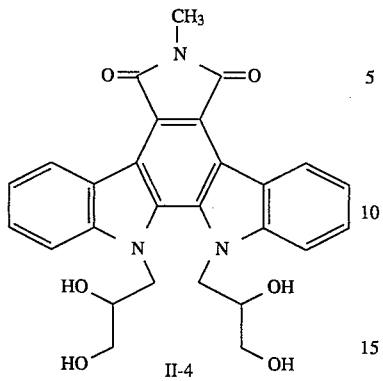

II-4

Preparation of Compounds I-9 and I-14

Compound (E) (see FIG. 8 and Japanese Published Unexamined Patent Application No. 295589/88) (49.3 mg, 0.1 mmol) was dissolved in 3 ml of dioxane, and then 0.1 ml of hydrazine hydrate was added thereto, followed by stirring at 110° C. for 2 hours. After evaporation of the solvent, methanol was added to the residue and the precipitates were collected by filtration to give 40 mg of Compound I-9.

$^1$H-NMR (CDCl$_3$)δ(ppm):1.19(3H, s),1.36(3H, s), 2.30 (3H, s), 2.45(1H, dd, J=5.0, 14.0Hz), 2.91(1H, dd, J=7.0, 14.0Hz), 4.10(1H, d, J-10Hz), 4.54(1H, d, J=10Hz), 6.63(1H, dd, J=5.0, 7.0Hz), 7.22–7.86(6H, m), 8.97(1H, d, J=8.0Hz), 9.25(1H, d, J=8.0Hz) SIMS(m/z):509(M+1)$^+$ Chromic acid (2.8 g, 28 mmol) was added to 20 ml of pyridine under ice cooling, and then 5 ml of pyridine containing 1.98 g (4 mmol) of Compound (F) (see FIG. 8 and Japanese Published Unexamined Patent Application No. 295589/88) was added thereto, followed by stirring at room temperature for 12 hours. After the solution was filtered through Celite, the solvent was evaporated, and the residue was subjected to silica gel column chromatography (chloroform) to give 0.98 g (Yield 48%) of Compound (G) see FIG. 8.

The following characteristic values for Compound (G) may be obtained by using NMR:

$^1$H-NMR(CDCl$_3$)δ(ppm):1.52(2.1H, s), 1.60(0.9H, s),2.32(0.9H,s), 2.36(2.1H,s), 2.67(1H, dd, J=5.0, 14.0Hz),3.09(2.1H,s), 3.38(0.9H,s) ,4.72–4.81(2H, m) ,6.72(1H,m), 7.20–9.32(8H,m)

Compound (G) (305 mg, 0.6 mmol) was dissolved in 6 ml of dimethylformamide, and then 36 mg (0.9 mmol) of sodium hydride (60%) was added thereto under ice cooling, followed by stirring at the same temperature for 10 minutes. Methyl iodide (0.056 ml, 0.9 mmol) was added thereto and the mixture was stirred at the same temperature for 30 minutes. A saturated aqueous solution of ammonium chloride (1 ml) and 10 ml of water were added to the solution and the precipitates were collected by filtration.

The product thus obtained was dissolved in a mixture of 25 ml of chloroform, 1 ml of methanol, and 1 ml of 3N HCl, and the solution was stirred at 60° C. for 10 minutes. The solution was washed with a saturated aqueous solution of sodium bicarbonate, and then 10 ml of tetrahydrofuran, 10 ml of methanol, and 1.5 ml of 2N NaOH were added to the organic layer, followed by stirring at room temperature for 10 minutes and evaporation of the solvent. After chloroform was added thereto for dilution, the mixture was washed successively with a 5% aqueous solution of citric acid and a saline solution, and dried over magnesium sulfate. After evaporation of the solvent, the residue was subjected to silica gel column chromatography (chloroform/methanol= 98/2) to give 102 mg (yield 36%) of Compound I-14. The following characteristic values for Compound I-14 may be obtained by using NMR and MS:

$^1$H-NMR(CDCl$_3$+DMSO-d$_6$'41)δ(ppm):2.24(3H,s) , 3.18(3H,s), 4.81(1H, t, J=6.0Hz), 6.83(1H, dd, J=5.0, 7.0Hz) ,7.24–8.08(6H,m),9.06(1H, d, J=7.0Hz), 9.25(1H, d, J=7.0Hz) EI-MS(m/z):467(M+1)$^+$ Preparation of Compounds I-15 and I-21

Figure 9:
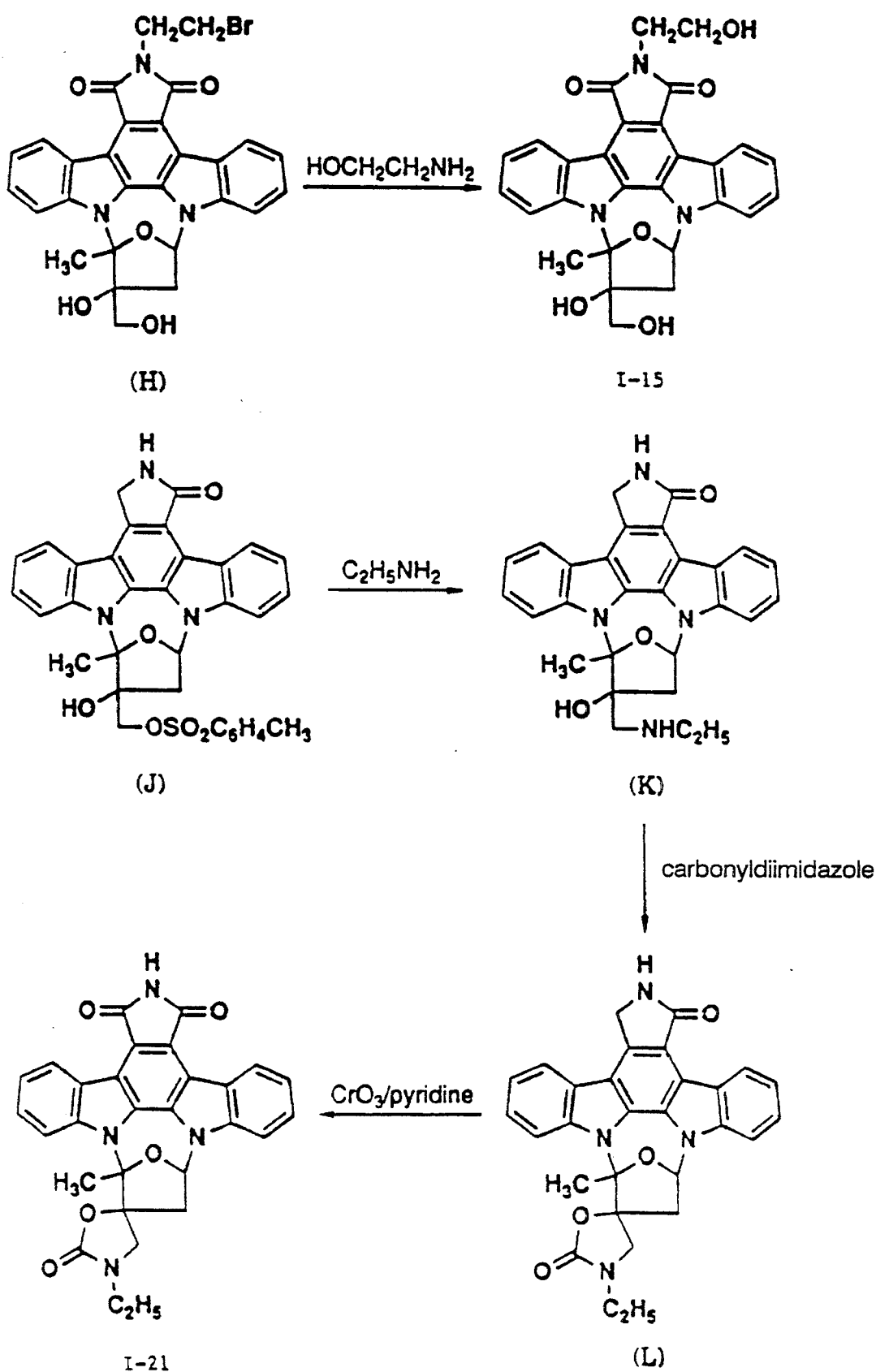
FIG. 9 is a figure outlining the chemical synthesis of compounds 1-15 and 1-21.

Compound (H) (see FIG. 9 and WO 88/07045) (112 mg, 0.2 mmol) was dissolved in 2 ml of dimethylformamide, and then 195 mg (2 mmol) of ethanolamine hydrochloride and 0.61 ml (4 mmol) of 1,8-diazabicyclo[5,4,0]-7-undecene were added thereto, followed by stirring at room temperature for 3 days. After evaporation of the solvent, the residue was subjected to silica gel column chromatography (chloroform/ methanol=98/2) to give 75 mg (yield 25%) of Compound I-15.

The following characteristic values may be obtained by using NMR and MS:

$^1$H-NMR(CDCl$_3$+DMSO-d$_6$; 4/1) δ(ppm):2.23(3H,s), 4.72(1H, t, J=5.0Hz),4.90(1H, t, J=5.0Hz), 5.41(1H,s), 6.89(1H, m),7.32–8.10(6H, m), 9.18(1H, d, J=7.0Hz),9.36(1H, d, J=7.0Hz)

SIMS (m/z) : 498 (M+i)$^+$

Compound (J) (see FIG. 9 and Japanese Published Unexamined Patent Application No. 155285/87) (890 mg, 1.5 mmol) was dissolved in 10 ml of dimethylformamide, and then 1.43 g (15 mmol) of ethylamine hydrochloride and 2.28 ml (15 mmol) of 1,8-diazabicyclo[5,4,0]-7-undecene were added thereto, followed by stirring at room temperature for 2.5 hours. To the solution was added 10 ml of water and the precipitates were collected by filtration to give 729 mg of Compound (K). See FIG. 9.

The following characteristic values may be obtained using NMR:

$^1$H-NMR (DMSO-d$_6$)δ(ppm):1.32(3H, t), 2.00–2.32(1H, m), 2.16(3H, s), 2.96–3.60(5H, m), 5.00(2H, s), 7.00–7.76(6H, m), 8.02(2H, t, J=8.0Hz), 8.58(1H, s), 9.18(1H, d, J=8.0Hz)

Compound (K) (650 rag, 1.39 retool) was dissolved in 7 ml of dimethylformamide, and then 675 mg (4.16 mmol) of carbonyldiimidazole was added thereto, followed by stirring for 3.5 hours under ice cooling. After 10 ml of water was added to the solution, the precipitates were collected by filtration and subjected to silica gel column chromatography (chloroform/methanol=97/3) to given 395 mg (yield 58%) of Compound (L). See FIG. 9.

The following characteristic values may be obtained using NMR:

$^1$H-NMR (CDCl$_3$)δ(ppm): 1.30(3H, t, J=7.0Hz), 2.30(2H,s), 2.68–2.96(2H, m), 3.44(2H, q, J=7.0Hz), 3.64 (1H, d, J=9.0Hz), 4.09(1H, d, J=9.0Hz) , 4.97(2H, s) , 6.45(1H, brs) , 6.76(1H, m), 7.20–8.08(7H, m), 9.32(1H, d, J=8.0Hz)

Chromic acid (0.49 g, 4.9 mmol) was added to 4 ml of pyridine under ice cooling, and then 2 ml of pyridine containing 345 mg of Compound (L) was added thereto, followed by stirring at room temperature for 12 hours. After the solution was filtered through Celite, the solvent was evaporated, and the residue was recrystallized from chloroform/methanol to give 272 mg (yield 77%) of Compound I-21.

The following characteristic values may be obtained by using NMR:

$^1$H-NMR(DMSO-$d_6$)δ(ppm):1.22(3H, t, J=7.0Hz), 2.28–2.80(1H, m), 2.36(3H, s), 3.12–3.60(3H, m), 3.86(1H, brd, J=10.0Hz), 4.22(1H, brd, J=10.0Hz), 7.16–8.00(6H, m), 9.04(1H, d, J=8.0Hz), 9.23(1H, d, J=8.0Hz)

Administration of K-252a Functional Derivatives

The compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; for oral administration, particularly in the form of tablets or capsules; or intranasally, particularly in the form of powders, nasal drops, or aerosols.

The composition may be conveniently administered in unit dosage form and may be prepared by any of the methods well known in the pharmaceutical art, or example, as described in *Remington's Pharmaceutical Sciences* (Mack Pub. Co., Easton, PA, 1980). Formulations for parenteral administration may contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of functional K-252a derivatives. Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration.

The materials of this invention can be employed as the sole active agent in a pharmaceutical or can be used in combination with other active ingredients, e.g., neurotrophins, or other factors (i.e., growth factors) or drugs which could facilitate neuronal survival or axonal growth in neurological diseases.

The concentration of a K-252a functional derivative described herein in a therapeutic composition will vary depending upon a number of factors, including the dosage of the K-252 functional derivative to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 μg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the neurological disease, the overall health status of the particular patient, the relative biological efficacy of the functional K-252a derivative selected, the formulation of the compound excipients, and its route of administration.

The present invention will be further illustrated by the following examples. These examples are not to be construed as limiting the scope of the invention, which is to be determined solely by the appended claims.

EXAMPLE 1

Neurotrophic activity of NT-3 was assayed by determining the choline acetyltransferase (CHAT) activity in basal forebrain cultures. NT-3 was added at the indicated concentrations after cells were plated for 2 hours to allow attachment to substrate. ChAT activity was measured after 5 days in vitro. NT-3 resulted in a dose dependent increase in ChAT activity in basal forebrain cultures with a maximum efficacy (1.5 to 2-fold increase) at 1000 ng/ml (FIG. 1). In serum-free media (see methods below), NT-3 was more efficacious (2 to 2.5-fold increase) at 1000 ng/ml (FIG. 1).

Methods: Basal forebrain cultures were prepared from E17 (Embryo Day 17) embryonic rats using trypsin dissociation. Basal forebrains were dissected and collected into hibernation medium consisting of 0.3 M $KH_2PO_4$, 20 mM sodium lactate, 195 mM sorbitol, 5 mM glucose, pH 7.4. The tissue was centrifuged 2 min at 50×g. After removal of the supernatant, the tissue was resuspended in 1 ml of 0.05% trypsin in calcium-free and magnesium-free Hanks Balanced Salt Solution (CMF-HBSS) and 10 mM HEPES pH 7.2, and incubated for 8 min at 37° C. Bovine serum albumin (BSA) (4%) in HBSS was added and the tube was centrifuged for 2 min. The pellet was resuspended in HBSS buffered containing 10 mM HEPES pH 7.2, 0.5% BSA and DNase. The tissue was mechanically dissociated using fire-polished Pasteur pipets, then passed through a sterile 53 μm Nitex filter and centrifuged through 5 ml of 4% BSA in HBSS. After resuspension of the pellet in culture medium, cells were counted with a hemocytometer. Cells were seeded at $4\times10^5$ cells/cm$^2$ on poly-1-ornithine coated plastic tissue culture 96-well plates in DMEM/F12 medium (50/50 v/v) with 5% horse serum and 0.5% fetal bovine serum. For serum-free conditions, N2 medium containing 0.05% bovine serum albumin (Bottenstein et al., *Proc. Natl. Acad. Sci. USA* 76:514-517, 1979) was used. Cells were incubated at 37° C. in a humidified atmosphere of 5% $CO_2$/95% air for 5 days. ChAT activity was measured using a modification of the Fonnum procedure (*J. Neurochem.* 24:407-409, 1975) according to the improvements of Ishida et al. (*J. Neurosci.* 3:1818-1823, 1983), McManaman et al. (*Dev. Biol.* 125:311-320, 1988), and Glicksman et al. (*J. Neurochem.* 61:210-221, 1993). Medium was removed completely from each well, and assay solution containing 0.1 M sodium phosphate, pH 7.4, 0.1% NP-40, 0.15 M NaCl, 1.5 mM choline chloride, 10 mM EDTA, 0.1 mM eserine sulfate, 3 mCi/ml [$^3$H]acetyl CoA and 100 mM acetyl CoA were added to each well and the plate was incubated at 37° C. for 1.5 hours. Samples were transferred to scintillation vials containing 1.5 ml of 0.1 M sodium phosphate buffer, pH 7.4, and 1.5 ml of scintillation cocktail (1.25 g/L tetraphenylboron, 200 ml acetonitrile, 800 ml toluene containing 32 ml/L PPO-POPOP). After vigorous shaking radioactivity in the non-aqueous phase was counted using a Packard Scintillation counter (Model 2500TR).

Recombinant rat NT-3 was produced using a recombinant baculovirus expression vector under the control of the polyhedron promoter (Fraser, In Vitro Cell. and Dev. Biol. 25: 225-235, 1989). The plasmid pXM-NT3 (Hallböök et al, Neuron 6: 845-858, 1991) containing the rat NT-3 cDNA clone was provided by Dr. Ira Black (University of Medicine and Dentistry of New Jersey, Piscataway, NJ). NT-3 cDNA was subcloned into transfer vector pVL1392 (obtained from InVitrogen Corp., San Diego, CA) for recombinant virus production. Recombinant baculovirus was produced by cotransfecting *Spodoptera frugiperda* insect cells (Sf-21) in monolayer with 1 μg of *Autographa californica* nuclear polyhedrosis virus DNA (InVitrogen or Baculogold™ by PharMingen, San Diego, CA) and 2–4 μg of the transfer vector by the calcium phosphate method of Smith et al. (*J. Virol.* 46:584-593, 1983). Recombinant plaques were verified as being recombinant by the hybridization of [$^{32}$p] labeled NT-3 sequences to blots of infected cell lysates (Summers and Smith, in *A Manual of Methods for Baculovirus Vectors and Insect Cell Culture Procedures* pp. 29–32, 1987). The recombinant virus was plaque-purified and amplified. The insect cell lines, *Trichoplusia ni* Tn-5B1-4 (InVitrogen Corp., San Diego, CA), were infected with recombinant baculovirus with a multiplicity of infection of 2 in 0.2 ml/cm$^2$ of Ex-Cell 401 (JRH Biosciences, Lenexa, KS). The conditioned medium containing NT-3 was harvested at 4 days postinfection. Approximately 1 liter of conditioned medium containing the NT-3 was centrifuged at 25,000×g for 15 min. The supernatant was then passed through a 1 cm×4 cm carboxymethyl-Sepharose Fast Flow column (Pharmacia, Piscataway, NJ) and after washing with column buffer (150 mM NaCl, 100 mM sodium phosphate pH 6.2), eluted with 250 mM NaCl$_2$ in 100 mM Tris·HCl pH7.6,° and then 500 mM NaCl in 100 mM Tris·HCl pH7.6. NT-3 was eluted in the 500 mM NaCl fractions. NT-3-containing fractions were identified by sodium dodecyl sulfate polyacrylamide gel electrophoresis (Laemmli, *Nature* 277:680-685, 1970) followed by silver staining to detect protein by the method of Morrissey (*Anal. Biochem.* 117:307-310, 1981) and pooled. These were then applied to a 4.6×250 mm Vydac reverse phase C4 column using a Rainin HPLC operating system. Following washing with both 0.1% trifluoacetic acid (TFA) and 5% (v/v) acetonitrile/ 0.1% TFA, NT-3 was eluted from a linear gradient of 5–65% acetonitrile in 0.1% TFA. NT-3-containing fractions were dried under vacuum in a Speed-Vac (Savant, Farmingdale, NY) without heating. NT-3 was resuspended in 10 mM acetic acid with 0.1% BSA and stored in aliquots at −70° C.

EXAMPLE 2

Figure 2:
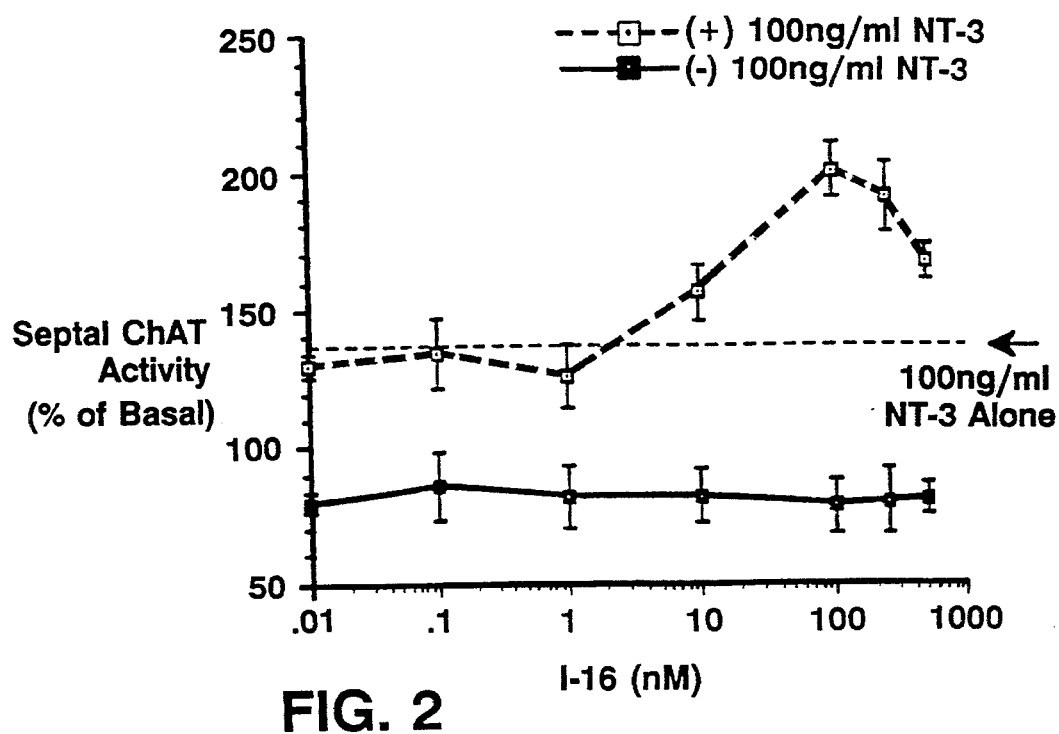
FIG. 2 is a graph which depicts the dosage effect of a representative K-252a functional derivative (I-16) and NT-3 on ChAT activity in embryonic rat basal forebrain cultures.
Figure 4:
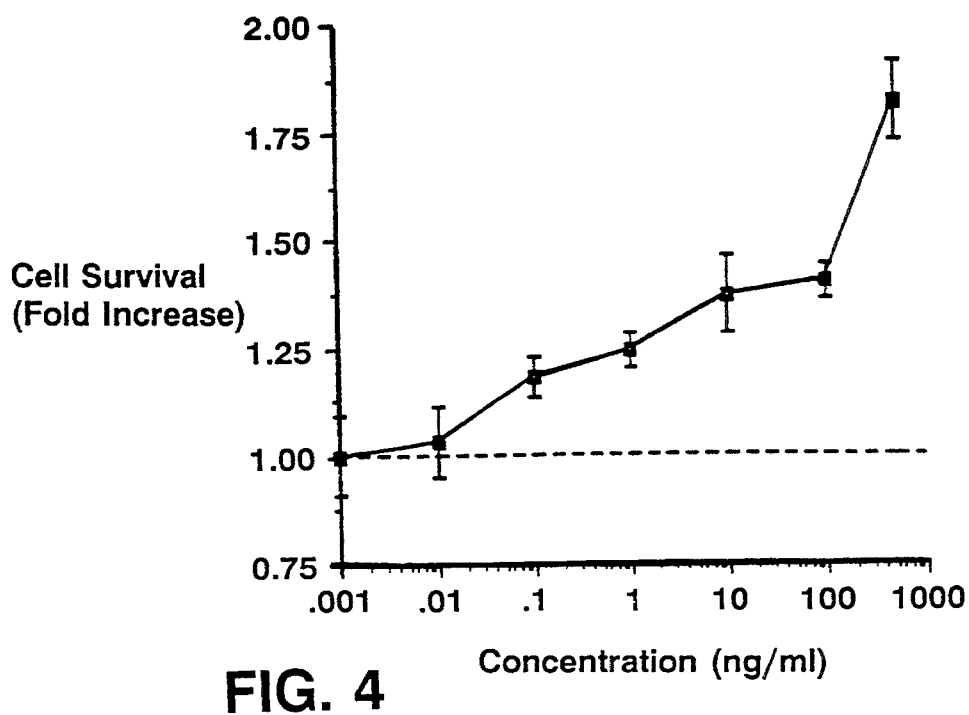
FIG. 4 is a graph illustrating the dosage effect of NT-3 on dorsal root ganglion neuron survival in vitro.

The ability of functional K-252a derivative 1-16 to potentiate NT-3 activity in basal forebrain cultures was determined using ChAT activity as a measure of cholinergic neuron function or survival. 1-16 alone had no effect on ChAT activity. However, 1-16 in the presence of NT-3, gave a dose dependent potentiation of ChAT activity (FIG. 2) to levels greater than those elicited by NT-3 alone. The results shown are the result of a single application of NT-3 and I-16 on the day of culture initiation, indicating a prolonged effect on the survival or function of basal forebrain cholinergic neurons. Methods were as detailed in Example 1.

EXAMPLE 3

Functional derivatives of K-252a were tested in the basal forebrain ChAT assay for ability to potentiate NT-3 activity. The data in FIG. 3 show that K-252a derivatives resulted in significant potentiation of NT-3 activity at one or more of the concentrations tested. Twenty-one of these derivatives show activity at 10 nM NT-3. In the presence or absence of serum the listed compounds enhanced ChAT activity over the ChAT activity elicited by NT-3 alone. The listed derivatives had no effect on ChAT activity in the absence of NT-3. The results show the result of a single application of NT-3 and the listed derivative on the day of culture initiation, indicating a prolonged effect on the survival or function of basal forebrain cholinergic neurons. Methods were as detailed in Example 1.

EXAMPLE 4

The effect of NT-3 on neuronal survival was assayed in dorsal root ganglion (DRG) cell cultures. Cell survival was measured by uptake of calcein AM (Molecular Probes, Eugene, OR), an analog of the dye, fluorescein diacetate. Calcein is taken up by cells and cleaved intracellularly by live cells to fluorescent salts that are retained by intact membranes of viable cells. Microscopic counts of viable neurons correlated directly with relative fluorescence values obtained using a fluorimetric viability assay method, described below. This method provides a reliable and quantitative measurement of cell survival. Dorsal root ganglion neuron survival was enhanced by NT-3 in a dose-dependent manner, with a maximal 1.6-fold over control at 50 ng/ml NT-3.

Methods: Dorsal root ganglia were dissected from embryonic age day 9 chick embryos (stage 35) and dissociated cells prepared by subsequent Dispase (neutral protease, Collaborative Research) dissociation. Neurons were seeded at low density (1.8×10$^4$ cells/cm$^2$) into 96-well poly-1-ornithine and laminin coated plates. Cells were cultured for 48 hours in serum-free N$_2$ medium containing 0.05% bovine serum albumin (Bottenstein et al., .supra) at 37° C. in a humidified atmosphere, 5%CO$_2$/95% air. Cell survival was assessed at 48 hours using a calcein viable fluorimetric assay. Calcein AM was diluted 2× in Dulbeccos phosphate buffered saline (DPBS) to 2× the final assay concentration (6 μM), and 100 μl was added to culture wells containing 100 μl of medium. The plates were then incubated for 1 hour at 37° C. Cells were then washed 4 times with PBS to remove excess calcein not taken up by cells. The plate was read using a Millipore plate reading fluorimeter (Cytofluor 2350) at emission=485 nm and excitation=538 nm. After subtraction of blank values (wells containing medium but no cells), relative fluorescent values reflect a quantitative measurement of cell survival in the predominantly (>95%) neuronal cultures (Bozyczko-Coyne et al., in press, 1993).

EXAMPLE 5

Figure 5:
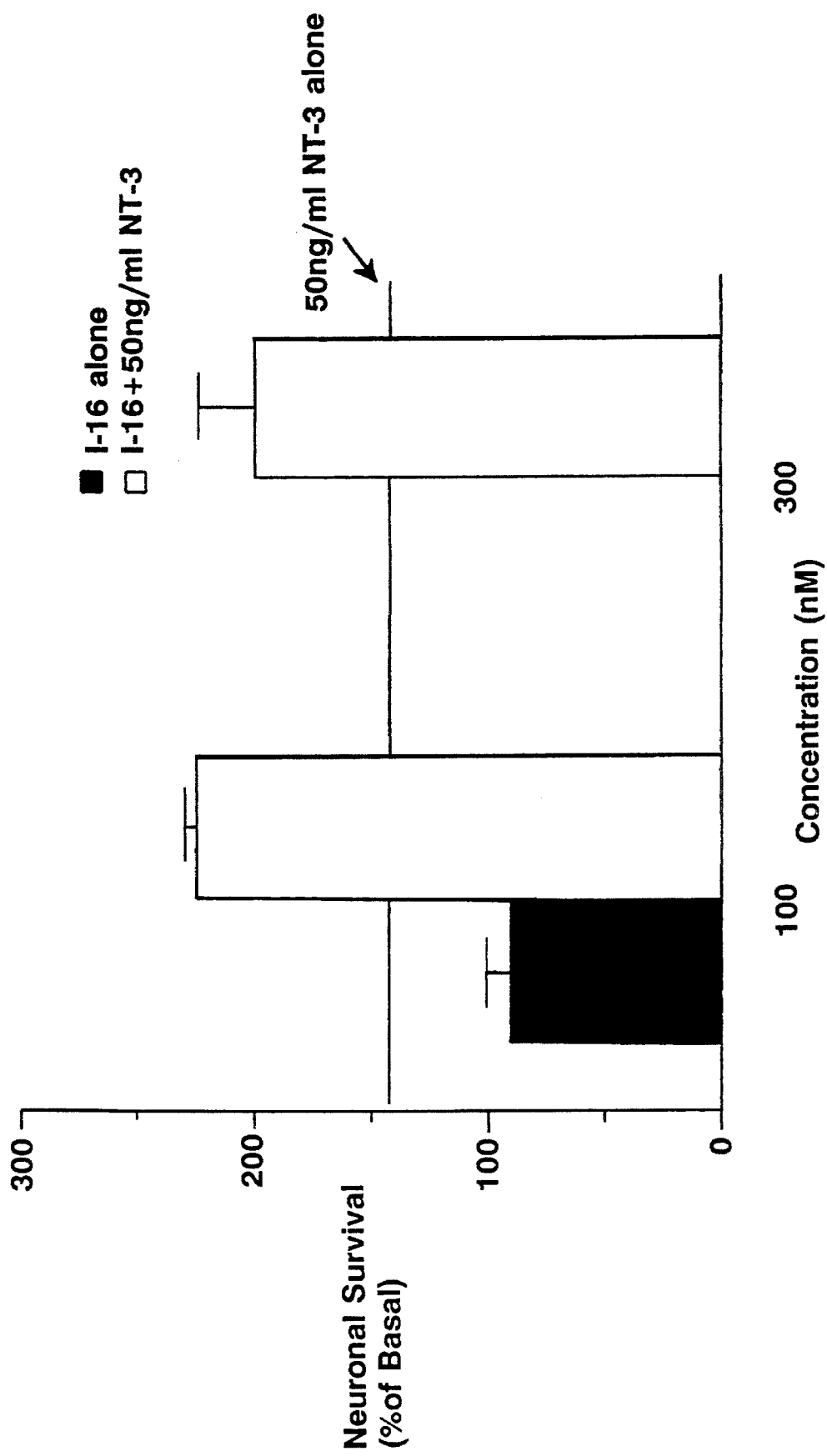
FIG. 5 is a graph illustrating the effect of NT-3 and a representative K-252a functional derivative (I-16) on dorsal root ganglion neuron survival in vitro.

In the absence of functional K-252a derivative 1-16, NT-3 elicited a 40% increase in DRG cell survival over untreated control cultures (FIG. 5). In the presence of 100 or 300 nM of I-16, there was a marked potentiation of the ability of NT-3 to promote DRG survival to values greater than 200% of untreated control cultures. In the absence of NT-3, I-16 had no effect on the survival of DRG neurons. Methods were as described for Example 4.

EXAMPLE 6

K-252a functional derivatives were tested in the DRG neuronal survival assay for ability to potentiate NT-3 activity. Derivatives tested at 100 nM resulted in significant potentiation of NT-3 activity. Compounds listed in FIG. 6 enhanced neuronal survival beyond the increase induced by NT-3 alone. The results shown are the result of a single application of NT-3 and the listed compounds on the day of culture initiation, indicating a prolonged effect on neuronal survival. Methods were as described in Example 4.

EXAMPLE 7

Figure 7:
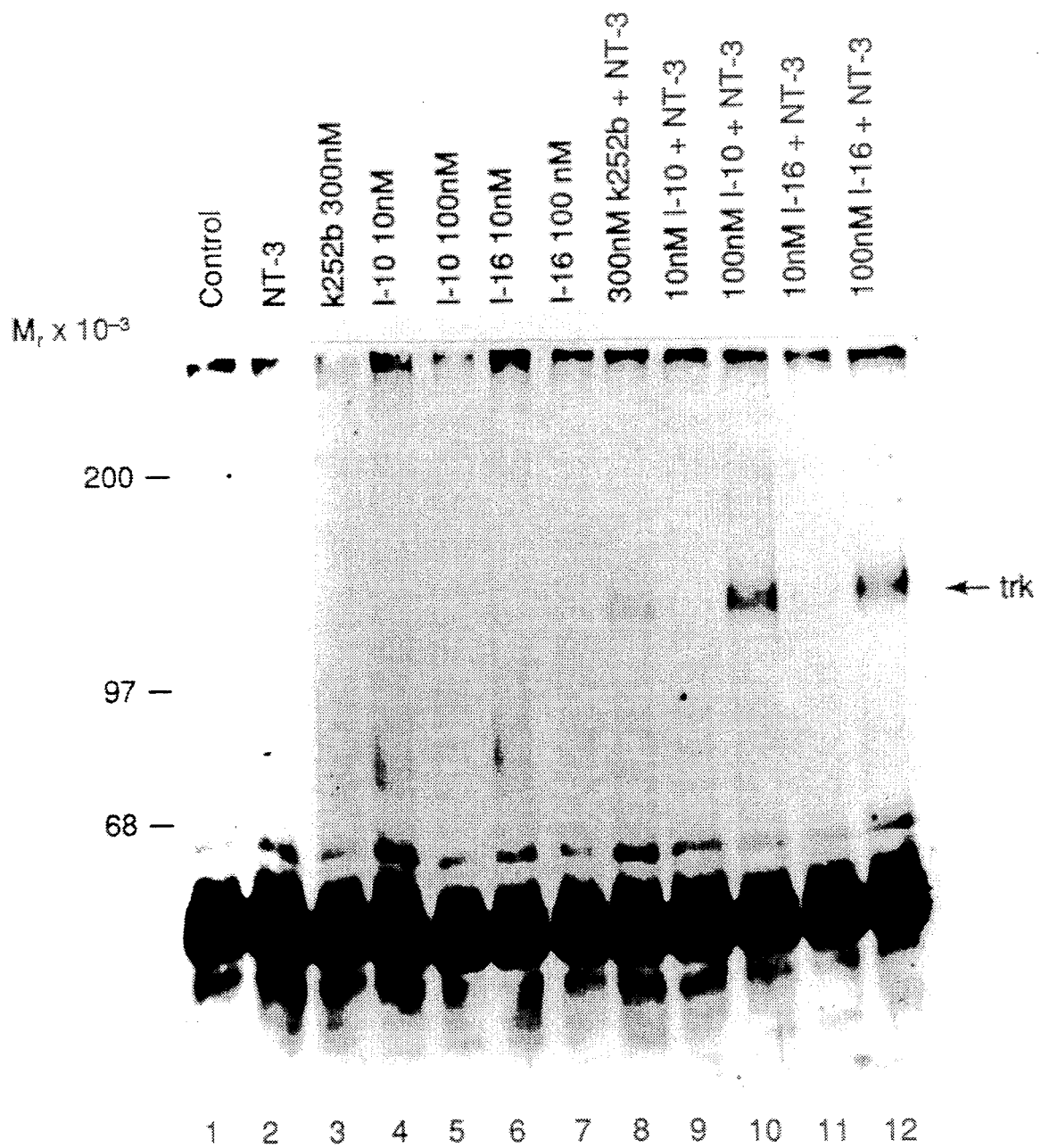
FIG. 7 is an immunoblot showing enhanced tyrosine phosphorylation of the trk cell receptor when PC-12 cells are contacted by a K-252a functional derivative.

Pheochromocytoma (PC-12) cells were incubated for 2 hours with vehicle (<0.1% DMSO) or a K-252a functional derivative. Cells were then incubated for 5 minutes in the absence or presence of NT-3. Cells were lysed and immunoprecipitated with anti-trk antibody. Proteins were separated by sodium dodecyl sulfate (SDS) polyacrylamide gel electrophoresis and transferred to polyvinylidene difluoride (PVDF) membrane. The membrane was immunoblotted with anti-phosphotyrosine antibody to allow visualization of tyrosine phosphorylated trk. No autophosphorylation of trk was observed in untreated cells (FIG. 7, lane 1). In the absence of any K-252a functional derivative, NT-3 did not elicit detectable tyrosine phosphorylation of trk (lane 2). Similarly, in the absence of NT-3, neither K-252b at 300 nM (lane 3) nor compounds I-16 or I-10 at 10 and 100 nM (lanes 4–7) caused autophosphorylation of trk. In combination, however, NT-3+300 nM K-252b (lane 8), or 100 nM compound I-10 (lane 10) or 100 nM compound I-16 (lane 12) resulted in a striking tyrosine phosphorylation of trk. Incubation of NT-3 with 10 nM compound I-10 or compound I-16 (lanes 9 and 11) yielded smaller but measurable increases in trk tyrosine phosphorylation.

Methods: PC-12 cells (obtained from American Type Culture Collection) were maintained in Dulbecco's Modified Eagle's Medium (DMEM) containing 2 mM glutamine, 7.5% horse serum, 7.5% fetal bovine serum, 1 mM sodium pyruvate and penicillin and streptomycin. Cells were incubated at 37° C. in a humidified atmosphere of 5% $CO_2$/95% air. Subconfluent cell monolayers were incubated at 37° C. for 2 hours in serum-free DMEM containing vehicle or K-252a functional derivative. Where indicated, NT-3 (50ng/ml) was added at 37° C. for 5 minutes. All samples including controls were exposed to 0.075% DMSO. To end the experiment, cells were rinsed with ice-cold phosphate-buffered saline (PBS) followed by lysis in RIPA buffer (1% Triton X-100, 1% sodium deoxycholate, 0.1% sodium dodecylsulfate, 150 mM sodium chloride, 10 mM Tris, pH 7.5, containing 20 ug/ml aprotinin, 1 mM phenylmethylsulfonyl fluoride (PMSF), 10 μM leupeptin and 1 mM sodium vanadate). Lysates were passed through a 26 gauge needle to shear DNA followed by a 15 minute centrifugation at 14,000×g. Supernatants were normalized to protein concentration. Anti-trk antibody was added to lysates, and after a 2 hour incubation at 4° C., the immune complex was collected on Protein A-Sepharose beads. Proteins were eluted from the beads with 4X Laemmli buffer (Laemmli, Nature 227:680-685, 1970), separated by sodium dodecyl sulfate polyacrylamide gel electrophoresis and transferred to PVDF membrane. The membrane was probed with anti-phosphotyrosine antibody (UBI). Antibody binding was visualized by enhanced chemiluminescence (ECL Kit, Amersham, Inc.).

Other embodiments are within the following claims.

What is claimed is:

1. A compound represented by the following formula:

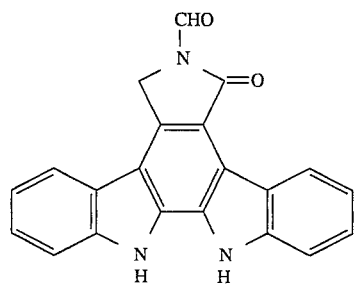

or a pharmaceutically acceptable salt thereof.

2. A compound represented by the following formula:

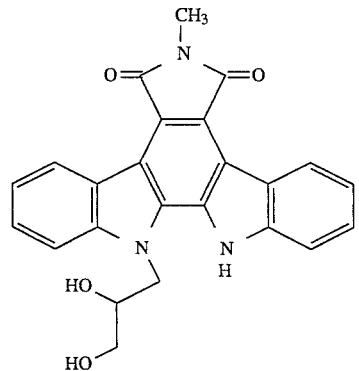

or a pharmaceutically acceptable salt thereof.

3. A compound represented by the following formula:

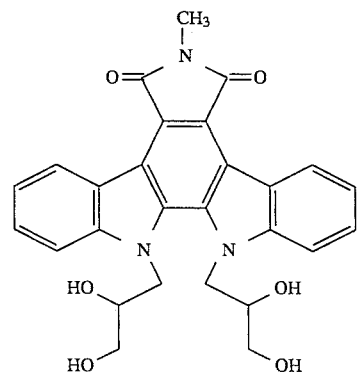

or a pharmaceutically acceptable salt thereof.

* * * * *

UNITED STATES PATENT AND TRADEMARK OFFICE
CERTIFICATE OF CORRECTION

PATENT NO.  : 5,468,872

DATED       : November 21, 1995

INVENTOR(S) : Marcie A. Glicksman, David P. Rotella, Nicola Neff, Chikara Murakata It is certified that error appears in the above-identified patent and that said Letters Patent is hereby corrected as shown below:

On the title page, item [54], replace the current title so it reads --K-252A FUNCTIONAL DERIVATIVES POTENTIATE NEUROTROPHIN-3 ACTIVITY FOR THE TREATMENT OF NEUROLOGICAL DISORDERS--;

On the title page, under "OTHER PUBLICATIONS", column 2, after "Lamballe et al.,", replace "trC" with line 35. --trkC--;

Column 1, line 2, in the title, replace the current title so it reads --K-252A FUNCTIONAL DERIVATIVES POTENTIATE NEUROTROPHIN-3 ACTIVITY FOR THE TREATMENT OF NEUROLOGICAL DISORDERS--;

Column 4, line 36, replace "H OH or $SC_2H_5$" to --H, OH, or $SC_2H_5$--;

Column 9, line 44, correct the spelling of "phosphorylation";

UNITED STATES PATENT AND TRADEMARK OFFICE
CERTIFICATE OF CORRECTION

PATENT NO. : 5,468,872

DATED : November 21, 1995

INVENTOR(S) : Marcie A. Glicksman, et al.

It is certified that error appears in the above-indentified patent and that said Letters Patent is hereby corrected as shown below:

Column 16, line 45, replace "(650 rag, 1.39 retool)" with --(650 mg, 1.39 mmol)--.

Signed and Sealed this

Twenty-sixth Day of March, 1996

Attest:

BRUCE LEHMAN

*Attesting Officer*   *Commissioner of Patents and Trademarks*